United States Patent [19]
Di Martini et al.

[11] 3,994,590
[45] Nov. 30, 1976

[54] DISCRETE FREQUENCY COLORIMETER

[76] Inventors: Raymond G. Di Martini, 106 Palisade Ave., Cliffside Park, N.J. 07010; Stephen Chopyak, 126 W. Grant St., Minneapolis, Minn. 55403

[22] Filed: Apr. 29, 1975

[21] Appl. No.: 572,928

[52] U.S. Cl. .............................. 356/178; 250/552; 250/565; 356/180; 356/205
[51] Int. Cl.$^2$ .......................................... G01J 3/46
[58] Field of Search ............ 356/73, 180, 181, 184, 356/190, 201, 205, 178; 250/552, 553, 573, 565

[56] References Cited
UNITED STATES PATENTS

| | | | |
|---|---|---|---|
| 2,324,304 | 7/1943 | Katzman | 250/573 |
| 3,263,553 | 8/1966 | Baruch | 356/184 |
| 3,588,253 | 6/1971 | Wittman | 356/93 |
| 3,727,066 | 4/1973 | Louderback et al. | 356/201 |
| 3,807,875 | 4/1974 | Fisher et al. | 250/552 |
| 3,831,030 | 8/1974 | Wrobel et al. | 250/552 |
| 3,910,701 | 10/1975 | Henderson et al. | 356/73 |

*Primary Examiner*—Vincent P. McGraw
*Attorney, Agent, or Firm*—Norman N. Popper

[57] ABSTRACT

A compact and portable colorimeter, including an integrally-formed probe having both a solid-state source of relatively monochromatic light and an optically coupled photodetector mounted therein. A power oscillator gating means is connected to the light source for pulsing same, to provide a chopped optical input. A demodulating circuit receives the output from the photodetector. The power oscillator gate signal is provided to a synchronous detector at the demodulating circuit, to synchronize detection with the chopping. The output from the demodulator is converted to a signal and read-out indicative of the concentration of that component of the sample which has absorbance characteristics correlated with the wavelength of the monochromatic source. The light source may comprise an LED, a laser diode or the like; and a tunable diode or array of LED's may also be used so as to enable a plurality of discrete frequency outputs, which outputs correlate with a plurality of chemical species the concentrations of which are to be determined.

8 Claims, 5 Drawing Figures

DISCRETE FREQUENCY COLORIMETER

BACKGROUND OF INVENTION

This invention relates generally to spectrophotometers, and more specifically relates to colorimeters of the type used for determining the presence and concentrations of chemical species in a liquid or gaseous sample containing such unknowns.

Highly sophisticated and complex spectrophotometers are widely used in the course of analyzing chemical systems. In a typical such device e.g. a wide-band source of light (e.g. in the visible or U-V spectrum) is processed through a monochromator, which may include a dispersion element such as a prism or grating, and an attendant wavelength drive mechanism for rotating the dispersion element to enable a series of wavelength outputs at relatively discrete frequencies. A sample subjected to analysis in such an instrument is traversed with a beam of light at successively varying wavelengths, and the resulting attenuation of the light beam is converted to a read-out indicative of the absorption or transmission characteristics of the sample. In many instruments of this type a so-called dual-beam mode of operation is employed — which while adding to the accuracy of the instrument, adds further complexity to the optical and electronic systems of the instrument.

Over the course of years, numerous colorimeters have been proposed, which are in essence highly simplified versions of the relatively sophisticated device described above. Interest in connection with these devices has centered, among other things, upon providing an instrument of relatively limited size and complexity, which might nevertheless provide accurate information with respect to at least certain absorption characteristics of a sample. Numerous of these prior art colorimeters have sought to incorporate or use a probe element, or similar means, which might be directly insertable into a liquid or gas sample, thereby eliminating the need for a cuvette assembly — together with the attendant problems of such assemblies.

Notwithstanding however, the considerable interest evidenced in providing colorimeters of the foregoing type, such instruments as have in the past been proposed, have not met with high commercial acceptance, and a need continues to exist for such an instrument.

In accordance with the foregoing, it may be regarded as an object of the present invention, to provide a highly accurate and dependable colorimeter, which is so compact as to be hand-holdable, and which includes a probe portion directly insertable into a liquid or gaseous sample.

It is a further object of the invention, to provide a compact and accurate colorimeter, which enables measurements of colorimetric properties at discrete frequencies, and without the necessity for conventional monochromaters, filters, or for complex mechanical or electronic light choppers.

It is yet a further object of the invention, to provide a hand-held colorimeter, which while eliminating the complex monochromators and electronic circuitry normally utilized in sophisticated spectrophotometers, enables a direct comparison between input and transmitted light levels, to thereby yield highly accurate results.

SUMMARY OF INVENTION

Now in accordance with the present invention, the foregoing objects, and others as will become apparent in the course of the ensuing specification, are achieved in a compact and portable colorimeter, which is hand-holdable and includes an integrally formed probe portion directly insertable into a liquid or gaseous sample. A solid state source of relatively monochromatic light is mounted at the probe, where such light source is optically coupled to a spaced photodetector, with the intervening space being accessible to the fluid sample. A power oscillator gating means is connected to the light source for pulsing same, to thereby provide a chopped optical input. A demodulator circuit receives the output from the photodetector. A signal from the power oscillator gate is also provided to a synchronous detector at the demodulator circuit, to synchronize detection with the chopping. The output from the demodulator is converted to a signal and a read-out indicative of the concentration of that component of the sample which has absorbance characteristics correlated with the predominant wavelength of the light source.

In a preferred embodiment of the colorimeter, the output from the demodulator circuit is provided as an input to a difference amplifier. The power oscillator gating means provides the other input to the difference amplifier. The levels of the inputs to the difference amplifier can be initially adjusted for balance in the presence of a reference sample, and since the output of the light source is proportional to its electrical input, the output of the difference amplifier is thereafter linearly related to the concentration of the chemical species to be measured in the sample.

The light source for the colorimeter may comprise an LED, a laser diode or the like. Further, a tunable diode or an array of LED's or other solid state sources may be used, so as to enable a plurality of discrete frequency optical outputs, which outputs correlate with a plurality of chemical species, the concentrations of which are to be determined.

BRIEF DESCRIPTION OF DRAWINGS

The invention is diagrammatically illustrated, by way of example, in the drawings appended hereto, in which.

DESCRIPTION OF PREFERRED EMBODIMENT

Figure 1:
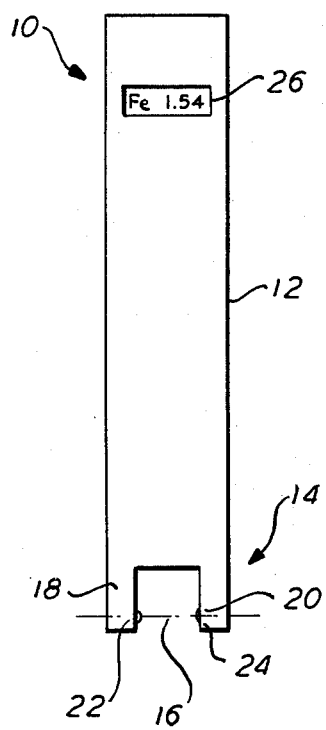
FIG. 1 is an elevation plan view of colorimeter apparatus in accordance with the present invention.

In FIG. 1 herein, an elevational simplified plan view appears, of a colorimeter 10 in accordance with the invention. The instrument is seen to be of substantially unitized construction, and includes a housing 12, the lower portion of which defines a probe 14, including a generally U-shaped opening 16. The lateral walls 18 and 20 abounding opening 16, respectively contain a light source 22 and a photodetector 24. The colorimeter 10 is a highly compact, hand-holdable unit, the height of the instrument being actually of the order of less than 6 inches. The light source 22 and photodetector 24, are thus very closely optically coupled, the spacing between the elements being typically of the order of 1 cm.

In accordance with a principal aspect of the invention, light source 22 comprises a pulsable solid state source of relatively monochromatic light. Preferably, for example, source 22 may comprise a light-emitting diode (LED). These LED's are, as is known to those familiar with the art, presently available in types displaying a wide variety of output frequencies, and devices of such type can be custom tailored so as to provide predominant outputs at wavelengths of interest for the present application.

Other solid state devices are also suitable for use as source 22, such as e.g., laser diodes. Similarly LED's of the so-called "tunable diode" type are highly suitable for the present application — particularly in that these latter devices are characterized in exhibiting a controllable change in spectral peak frequency in accordance with a control signal provided thereto. Such devices are available from several sources, such as e.g. Texas Instruments, and Siemens.

Photodetector 24 is also a solid state photoreceptor, such as a PIN diode or other PN junction photodiode. Similarly, avalanche photodiodes, phototransistors, phototransistors, photo FET's, and other devices, including cadmium sulfide cells, may be used as the photodetector 24.

Because of the very close optical coupling between light source 22 and photodetector 24, no complex photomultiplier tube or other complex amplification schemes are required in the present invention. Since in particular, virtually all light generated by source 22 is usable, the light density received at photodetector 24 is high enough to be measured with the relatively simple solid state devices above-mentioned. The extremely close spacing between source 22 and photodetector 24 also is instrumental in enabling the "cuvetteless" configuration depicted, wherein probe 14 is directly insertable, e.g. into a liquid sample. In particular the present arrangement requires no auxiliary optics — although small focusing and condensing lenses may be incorporated in the coupling path between light source and photodetector, to somewhat increase the efficiency of the instrument.

Colorimeter 10 may include external OFF-ON and balancing controls, and also may include external controls for varying the wavelength output utilized during a sample reading, in accordance with the chemical species being evaluated in the sample. None of these controls explicitly appear in the simplified drawing of FIG. 1. A read-out display 26 indicates the concentration of the species being examined in the sample, upon the instrument being inserted into the sample body, and suitably activated. Typically the read-out is provided as a visual display — in terms of concentration of the species in moles/liter, in parts per million etc., and does not per se form part of the present invention. For example, segment lamps, liquid crystal displays, or other alpha-numeric displays are utilizable.

Figure 2:
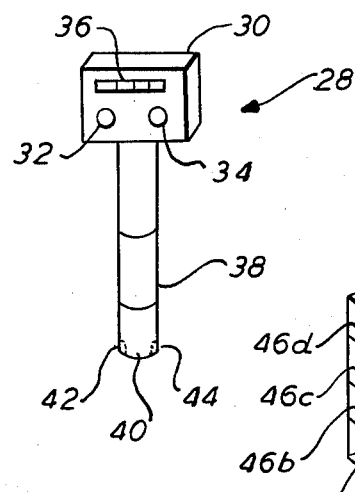
FIG. 2 is a simplified perspective view of a further external arrangement suitable for the invention.

In FIG. 2 a simplified perspective view appears of a further external arrangement suitable for the invention. The colorimeter 28 therein shown is similar to colorimeter 10, although in this instance an upper casing 30 includes the bulk of electronic circuitry, and also carries external balance controls 32 and 34, and read-out scale 36. A probe 38 extends downwardly, is open at its lower end 40, and carries the spaced light source 42 and photodetector 44.

Figure 3:
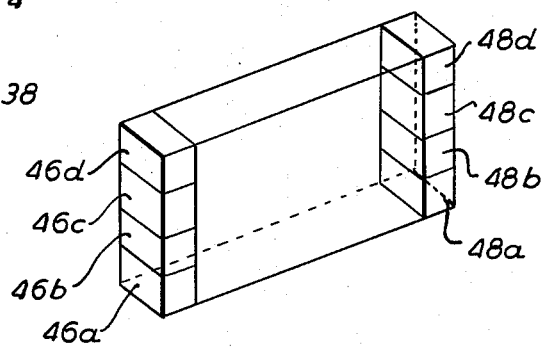
FIG. 3 is a highly schematic view of a probe tip useful with the invention, wherein a plurality of solid state light sources are coupled with a corresponding number of photodetectors.

In FIG. 3 a schematic perspective view appears, of a probe tip useful with the invention. In this instance a series or array 46a, 46b, 46c, and 46d of light sources are provided, each said source being in optically coupled arrangement with a photodetector 48a, 48b, 48c, and 48d. Each source 46a, etc. of the array may comprise an LED, and each such source has a spectral peak output at a specific wavelength — differing from that of its neighbor. The wavelength outputs are individually correlated with specific chemical species, so that by activating the sources sequentially the signals provided by the corresponding photodetectors 46a etc. (which may be PIN diodes or so forth) enable a source of read-outs of the concentrations of the associated chemical species. Thus, e.g., the source 46a may provide a spectral peak output at a wavelength corresponding to strong absorption by ferrous ion, and so forth. When the multi-channel type probe of FIG. 3 is utilized, suitable elements are, of course, incorporated into the associated electronics circuitry to enable manual or automatic scanning among the light source - photodetector pairs.

Figure 4:
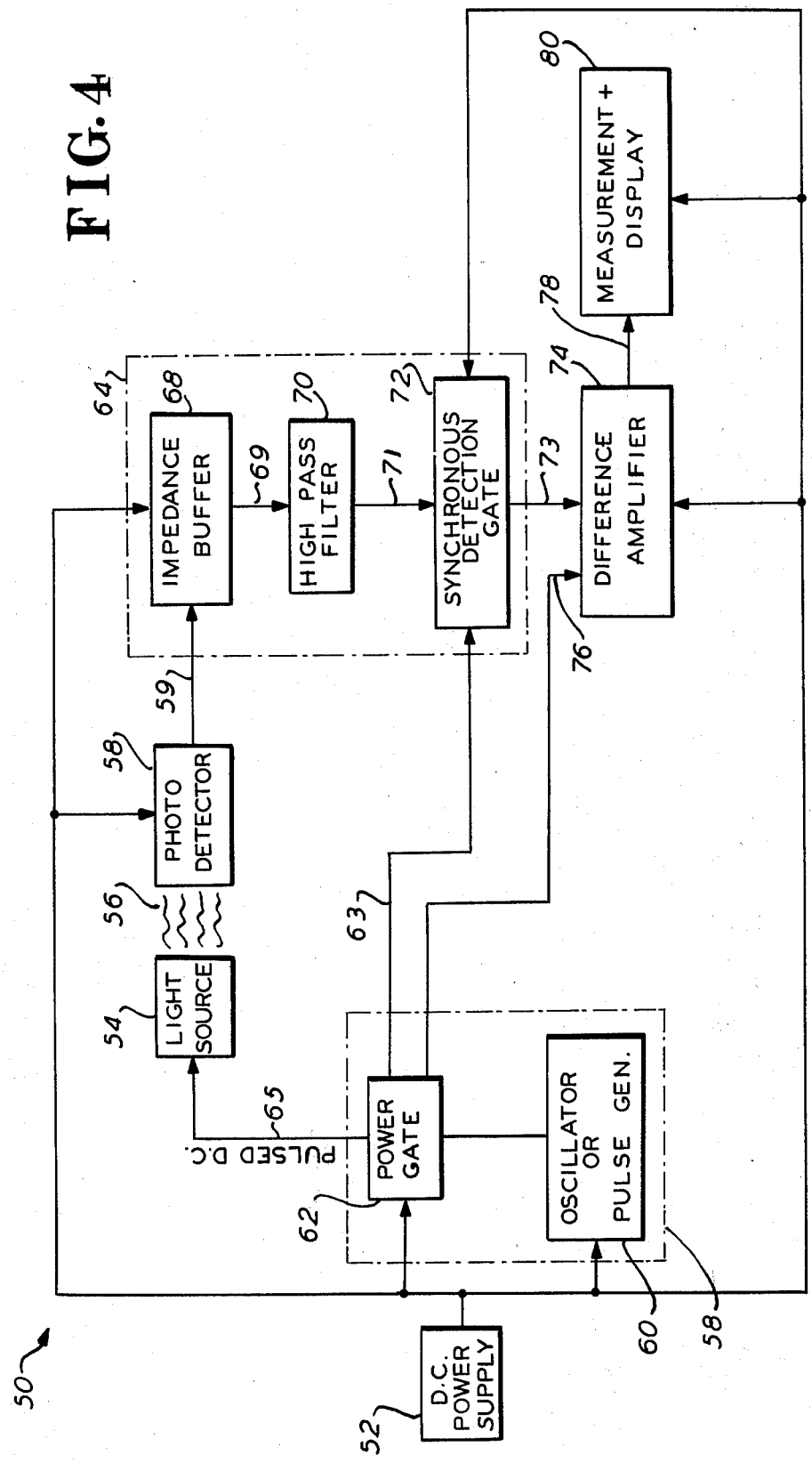
FIG. 4 is an electrical block diagram setting forth the basic operarion of a preferred circuit for use with the invention.

In FIG. 4 an electrical block diagram appears, setting forth the basic operation of a preferred circuit 50 for use with the invention.

In this circuit 50, a D.C. power supply 52, which may be battery energized, furnishes power at various potential levels to all other components of the system. In accordance with the invention, the light source 54, comprising e.g. the LED source previously mentioned, is optically coupled via sample path 56, to photodetector 58. Light source 54 is powered by the power oscillator gate 58, consisting of an oscillator (or pulse generator) 60, and a power gate 62. Oscillator 60 serves to provide a time reference for the system, and determines the chopping of the pulsing frequency for light source 54.

Power gate 62 effectively comprises an electronic chopper for light source 54. In particular, utilizing the input signal from oscillator 60, gate 62 provides a train of pulses to light source 54, which, assuming the latter to be an LED, are current pulses. Because the optical output of the LED is linearly proportioned to the current input it will be evident that the optical output (to sample path 56) is proportional to the height of the current pulses. A signal is, further, simultaneously taken from power gate 62 and provided to synchronous detection gate 72.

The photodetector 58 provides at its output 59, a pulsed D.C. signal, of magnitude proportional to the coupled light at path 56. This signal also includes noise components arising from electrical interaction and from spurious light and so forth. The signal is provided to demodulator and conditioner circuit 64, where it is first passed to an impedance buffer 68 which isolates the photodetector from the remainder of the circuit so that the measuring process does not affect the signal magnitude. Some amplification may optionally be utilized here, depending upon the specific choice of light source and photodetector, and on the optical coupling therebetween.

The output 69 from impedance buffer 68 is passed through a high pass filter 70, which blocks undesired D.C. components of the signal. The output at 71 is thus a train of pulses, of magnitude proportional to the transmission through the coupling sample path 56.

The conditioned output at 71 is then provided to synchronous detection gate 72, which is phase-locked to power gate 62 via the signal coupled through line 63. This phase-locking serves to eliminate the possibility of detecting and passing on spurious signals, and noise, such as e.g. spurious signals arising from ambient, background light, or so forth. The signal at output 73 is thus relatively free of noise and undesired components, and it is this signal which is now provided to difference amplifier 74.

Difference amplifier 74 has provided thereto as its other input 76, a signal corresponding to that provided (via line 65) to light source 54. Accordingly the difference amplifier 74 compares the input to light source 54, directly to the output 73 from synchronous detection gate 72. Since the output from light source 54 is proportional to its electrical input, the difference measurement gives an output 78 directly proportional to the light absorbed by the test specimen (or whatever other material) is present at the sample path 56. This output 78, in the form of a train of pulses, is thereupon provided to measurement and display circuits 80, which converts such output to a signal indicative of the transmission and/or absorbance of the test sample; and may further convert the said output to a signal and read-out directly indicative of the concentration of that component of the sample having absorbance characteristics correlated with the predominant wavelength of the light source 54. Techniques for converting the difference signal output 78 into transmission or absorbance signals are wellknown and not per se of the present invention; accordingly, details regarding such techniques are not set forth herein.

It will be appreciated that the circuit arrangement above set forth, automatically provides an electronic reference signal in that the signal in line 76 is indeed proportional to the light projected into sample path 56 — and is also phase-locked to the comparing signal of line 73. In practice the colorimeter may initially be balanced by means of a potentiometer in the signal processing line, such potentiometer being adjusted to indicate 100% transmission (or "0" absorbance) for the condition where a sample devoid of the chemical species of interest is present in sample path 56.

Figure 5:
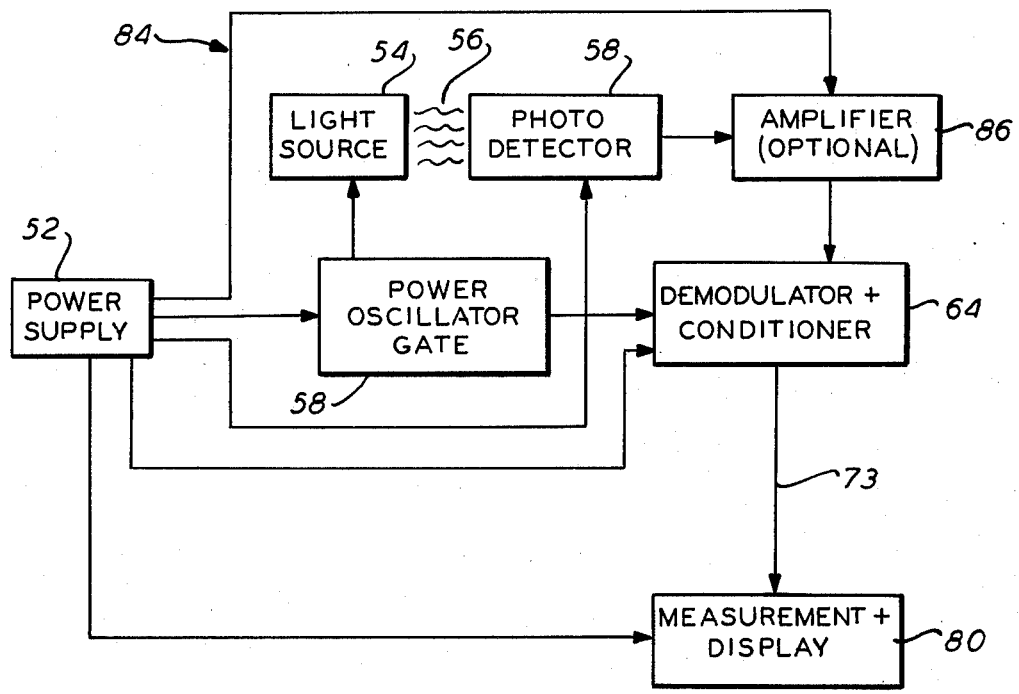
FIG. 5 is an electrical block diagram illustrating an alternate circuit arrangement suitable for the invention.

In FIG. 5, a simplified electrical block diagram appears, illustrating an alternate circuit 84 suitable for use with the invention. This circuit 84 includes a series of elements identified by reference numerals in correspondence to identically performing blocks in FIG. 4. An amplifier 86 is shown separately from the demodulator and conditioner block 64 — this optional stage of amplification has already been discussed in connection with FIG. 4. A more noteworthy distinction, however, is the absence of the difference amplifier 74 (of FIG. 4). For the FIG. 5 embodiment, no direct comparison of the output 73 is thus made with a reference-correlated signal. In general therefore, the arrangement of FIG. 5 is nor as accurate or dependable as the highly effective circuit of FIG. 4, but the simplified circuit 84 is yet fully adequate for many low-cost applications, where a lesser degree of precision can be tolerated.

While the present invention has been particularly set forth in terms of specific embodiments thereof, it will be understood in view of the present specification, that numerous variations upon the invention are now enabled to those skilled in the art, which variations yet reside within the scope of the present teaching. Accordingly, the invention is to be broadly construed, and limited only by the scope and spirit of the claims now appended hereto.

We claim:

1. A compact and portable colorimeter comprising in combination:

a casing including an integrally-formed probe portion;

a pulsable solid state source of relatively monochromatic light mounted in said probe;

photodetector means at said probe, said detector means being optically coupled to said light source through a sample receiving path at said probe;

a power oscillator gating means connected to said light source for pulsing same to thereby provide a chopped optical input during a colorimetric measurement of said sample;

a demodulating circuit including synchronous detector means, being connected to receive the output from said photodetector means, said power oscillator gate signal being provided to said demodulator means to synchronize the rate of detection with the rate of said chopping;

a difference amplifier connected to receive the output from said demodulator circuit means as one input thereto; the other input to said difference amplifier being provided from said power oscillator gating means, and the levels of said inputs being initially adjustable for balance at said difference amplifier in the presence of a reference sample, whereby the output from said difference amplifier is linearly related to the concentration of the chemical component to be measured in said samples; and measurement and read-out means for converting the output from said difference amplifier to a signal and read-out indicative of at least one of either the absorbance or transmission of said sample with respect to the wavelength of said monochromatic light.

2. Apparatus in accordance with claim 1, wherein said measurement and read-out means converts the output from said demodulator circuit to a signal and read-out indicative of the concentration of that component of said sample having absorbance characteristics correlated with the wavelength of said monochromatic light.

3. Apparatus in accordance with claim 1, wherein said light source comprises a light emitting diode providing an optical output at a narrow wavelength range determinatively related to the absorption characteristics of the chemical component to be measured in said sample.

4. Apparatus in accordance with claim 1, wherein said light source comprises a diode laser providing an optical output at a narrow wavelength range determinatively related to the absorption characteristics of the chemical component to be measured in said sample.

5. Apparatus in accordance with claim 1, wherein said light source comprises a tunable diode, and wherein said colorimeter includes control circuit means for selectively varying the optical output from said diode to provide an optical output at a narrow range determinatively related to the absorption characteristics of the chemical component to be measured in said sample.

6. Apparatus in accordance with claim 1, including a plurality of discrete solid state light sources mounted at said probe; each said source providing an optical output predominantly at a predetermined wavelength, whereby to provide a series of optical outputs at differing discrete wavelengths.

7. Apparatus in accordance with claim 6, including at said probe a plurality of photodetectors, each of said photodetectors being optically coupled to one each of said light sources.

8. Apparatus in accordance with claim 6, wherein said light sources are light-emitting diodes.

* * * * *